United States Patent [19]

Gardner et al.

[11] 4,442,098

[45] Apr. 10, 1984

[54] PENTACYCLIC DERIVATIVES OF PIPERAZINE

[75] Inventors: Derek V. Gardner, Bishop Stortford; Laramie M. Gaster, Sawbridgeworth, both of England

[73] Assignee: Beecham Group Limited, England

[21] Appl. No.: 332,347

[22] Filed: Dec. 18, 1981

[30] Foreign Application Priority Data

Dec. 31, 1980 [GB] United Kingdom ............... 8041558

[51] Int. Cl.³ ............... C07D 471/06; C07D 498/06; C07D 513/06; A61K 31/495
[52] U.S. Cl. ............... 424/248.51; 424/250; 424/248.56; 424/248.57; 260/243.3
[58] Field of Search ............... 260/243.3, 72, 244.4; 544/245, 342; 424/250, 248.51, 248.56, 248.57

[56] References Cited

U.S. PATENT DOCUMENTS 3,534,041 10/1970 Van der Burg ............... 424/250 X
3,701,778 10/1972 Van der Burg ............... 424/250 X

FOREIGN PATENT DOCUMENTS 1173783 12/1969 United Kingdom .
1229252 4/1971 United Kingdom .

Primary Examiner—Donald G. Daus
Assistant Examiner—William A. Teoli, Jr.
Attorney, Agent, or Firm—Jacobs & Jacobs

[57] ABSTRACT

Compounds of formula (I):

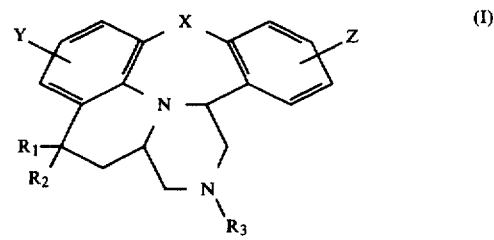

wherein:
X is $CH_2$, O, S or NR wherein R is hydrogen or $C_{1-4}$ alkyl;
Y and Z are independently selected from hydrogen, $C_{1-4}$ alkyl, $C_{1-4}$ alkoxy, halogen or $CF_3$;
$R_1$ is hydrogen, $C_{1-6}$ alkyl, phenyl or phenyl-$C_{1-4}$ alkyl any of which phenyl moieties may be substituted by one or more of $C_{1-6}$ alkyl, $C_{1-6}$ alkoxy, halogen or $CF_3$;
$R_2$ is hydrogen, OH, $C_{1-6}$ alkoxy, phenyl-$C_{1-4}$ alkoxy, $C_{1-7}$ acyloxy or $NR_4R_5$ wherein $R_4$ and $R_5$ are independently selected from hydrogen or $C_{1-6}$ alkyl; $R_4$ is hydrogen and $R_5$ is OH or $C_{1-4}$ alkoxy; or $R_4$ and $R_5$ together form $C_{3-6}$ polymethylene optionally interrupted by O or $NR_6$ where $R_6$ is hydrogen or $C_{1-4}$ alkyl; or together with $R_1$ forms an oxo group or $=NOR_7$ wherein $R_7$ is hydrogen or $C_{1-6}$ alkyl; and
$R_3$ is hydrogen or $C_{1-6}$ alkyl have useful pharmacological activity, processes for their preparation and their use.

8 Claims, No Drawings

PENTACYCLIC DERIVATIVES OF PIPERAZINE

This invention relates to compounds having mood modifying, particularly anti-depressant and anxiolytic activity, to pharmaceutical compositions containing them and to processes for their preparation.

U.K. Pat. No. 1 173 783 describes and claims compounds of formula (A):

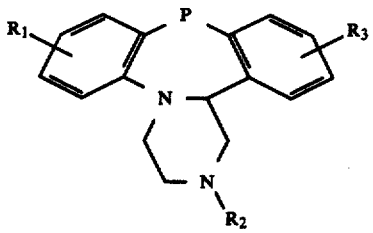

wherein:
$R_1$ and $R_3$ represent a hydrogen or halogen atom, a hydroxy, lower acyloxy, alkyl of alkoxy group, or a trifluormethyl group;

$R_2$ represents hydrogen, a lower alkyl or aralkyl group, an aminoethyl or aminopropyl group N-substituted by one or more lower alkyl groups, or a lower alkyl group forming a substituent of an N-containing heterocyclic ring, the said ring being directly bonded to the nitrogen atom or the piperazine ring, and P represents a single bond, or a methylene, ethylene or —CH=CH— group.

U.K. Pat. No. 1 229 252 describes and claims compounds of formula (B):

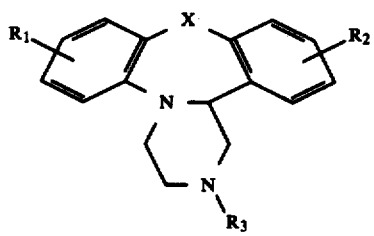

wherein:
$R_1$ and $R_2$ represent hydrogen, halogen, hydroxyl, acyloxy, alkyloxy or alkyl having 1–6 carbon atoms, or trifluoromethyl groups;

$R_2$ represents hydrogen, an alkyl group having 1–6 carbon atoms, an aralkyl group with 7–12 carbon atoms, an aminoethyl or aminopropyl group which, if desired, can be substituted in the N-position by an alkyl group with 1–6 carbon atoms, or an alkyl group having 1–6 carbon atoms and a nitrogen-containing heterocyclic ring; and X represents oxygen, sulphur, or

with $R_4$ representing an alkyl group having 1–6 carbon atoms.

We have now discovered a structurally distinct class of compounds which also have mood-modifying activity.

The present invention provides compounds of formula (I) and pharmaceutically acceptable salts thereof:

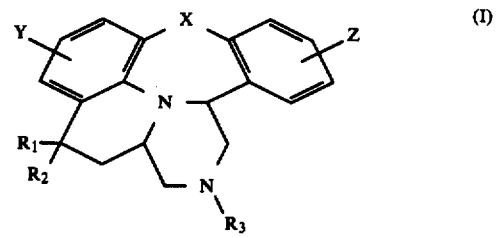

wherein:
X is $CH_2$, O, S or NR wherein R is hydrogen or $C_{1-4}$ alkyl;

Y and Z are independently selected from hydrogen, $C_{1-4}$ alkyl, $C_{1-4}$ alkoxy, halogen or $CF_3$;

$R_1$ is hydrogen, $C_{1-6}$ alkyl, phenyl or phenyl-$C_{1-4}$ alkyl any of which phenyl moieties may be substituted by one or more of $C_{1-6}$ alkyl, $C_{1-6}$ alkoxy, halogen or $CF_3$;

$R_2$ is hydrogen, OH, $C_{1-6}$ alkoxy, phenyl-$C_{1-4}$ alkoxy, $C_{1-7}$ acyloxy or $NR_4R_5$ wherein $R_4$ and $R_5$ are independently selected from hydrogen or $C_{1-6}$ alkyl; $R_4$ is hydrogen and $R_5$ is OH or $C_{1-4}$ alkoxy; or $R_4$ and $R_5$ together form $C_{3-6}$ polymethylene optionally interrupted by O or $NR_6$ where $R_6$ is hydrogen or $C_{1-4}$ alkyl; or together with $R_1$ forms an oxo group or $=NOR_7$ wherein $R_7$ is hydrogen or $C_{1-6}$ alkyl; and $R_3$ is hydrogen or $C_{1-6}$ alkyl.

When X is NR, suitable values for R include hydrogen, methyl or ethyl, preferably methyl. Often X will be $CH_2$.

Suitable values of Y and Z include hydrogen, methyl, ethyl; methoxy and ethoxy; fluoro, chloro and bromo; and $CF_3$. Favourably both Y and Z will be hydrogen. Y when other than hydrogen is preferably in the 8-position, ie para to the piperazine nitrogenatom. Suitable values for $R_1$ include hydrogen, methyl, ethyl, n- and iso-propyl; n, sec- and tert-butyl; phenethyl, benzyl or phenyl any of which phenyl moieties may be substituted by one or more of methyl, ethyl, n- and iso-propyl; methoxy, ethoxy, n- and iso-propoxy; fluoro, chloro, bromo or $CF_3$. Favourably $R_1$ is hydrogen, methyl, phenyl or benzyl. Often $R_1$ will be hydrogen.

Suitable values for $R_2$ include hydrogen, OH, methoxy, ethoxy, n- and iso-propoxy, benzyloxy, n- sec, and tert-butoxy; acetoxy, propionyloxy, n- and iso-butyryloxy or $NR_4{}^1R_5{}^1$ wherein $R_4{}^1$ and $R_5{}^1$ are independently selected from hydrogen, methyl, ethyl, n and iso-propyl; or n-, sec- and tert-butyl; $R_4$ is hydrogen and $R_5$ is OH or $OCH_3$ or $R_4$ and $R_5$ together form —$(CH_2)_4$—, —$(CH_2)_5$—, —$(CH_2)_2$—O—$(CH_2)_2$— or —$(CH_2)_2$—$NR_6$—$(CH_2)_2$—

Favourably $R_3$ include hydrogen, methyl, ethyl, n- and iso- propyl; and n-, sec- and tert-butyl. Preferably $R_3$ is methyl.

There is a group of compounds within formula (I) wherein Y and Z are both hydrogen, $R_1$ and $R_2$ are as defined in formula (I) except that they do not together form oxo or =NOR₇ and X and R₃ are as defined in formula (I).

A favourable sub-group of compounds within formula (I) is of formula (II) and pharmaceutically acceptable salts thereof:

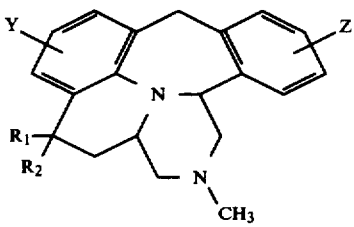

(II)

wherein R₁ and R₂ are as defined in formula (I).

Suitable and preferred values for R₁ are as described under formula (I).

Within formula (II) there is a preferred sub-group of compounds of formula (III):

(III)

wherein:
R₁¹ is hydrogen, methyl, phenyl or benzyl;
R₂¹ is hydroxy, methoxy, acetoxy or benzyloxy; and
Y is as defined in formula (I).

Suitable and preferred values for Y are as defined in formula (I).

Preferably R₁¹ will be hydrogen and R₂¹ will be hydroxy.

One particularly preferred compound of this invention therefore is 1,2,3,3a,4,5,9,13b-octahydro-2-methyl-2-benzazepino[4,3,2-ij]pyrazino[1,2-a]quinolin-5-ol.**
**(ie the compound of formula (III) above wherein R¹₁ is H and R¹₂ is hydroxy).

Another suitable sub-group of compounds within formula (II) is of formula (IV):

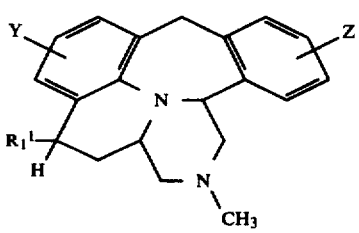

(IV)

wherein:
R₁¹ is hydrogen, methyl, phenyl or benzyl; Often R₁¹ will be hydrogen.

A further sub-group of interest is of formula (V):

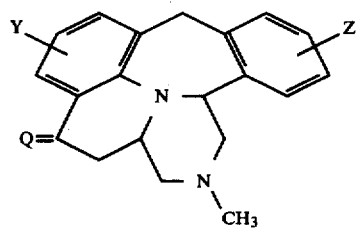

(V)

wherein:
Q is oxygen or NOR₇ wherein R₇ is as defined in formula (I).

A further sub-group of interest is of formula (VI):

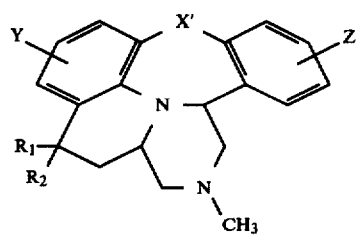

(VI)

wherein:
X' is O or S and R₁ and R₂ are as defined in formula (I).

Another sub-group of interest is of formula (VII):

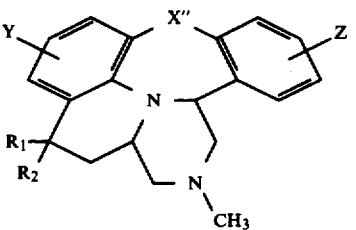

(VII)

wherein:
X" is NR as defined in formula (I) and R₁ and R₂ are as defined in formula (I).

Suitable and preferred values of R₁ and R₂ are as described under formula (I).

Compounds of the formula (I) have more than one asymmetric centre and are capable of existing in a number of stereoisomeric forms. The invention extends to each of these forms and to mixtures thereof (including racemates). The isomers may be separated from one another using conventional techniques, such as chromatography. (These compounds hereinafter referred to as the 'A' series isomers are generally preferred.)

Suitable examples of salts of the compounds of formula (I) include acid addition salts with pharmaceutically acceptable inorganic and organic acids, such as hydrochloric, hydrobromic, sulphuric, maleic and succinic acids.

The invention also provides a process for the preparation of a compound of formula (I) which process comprises the cyclisation of a compound of formula (VIII) or a salt thereof:

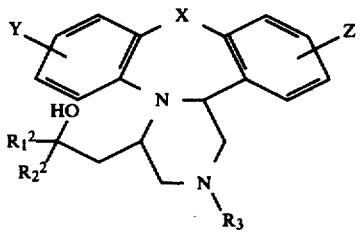

(VIII)

wherein $R^2_1$ is hydrogen, $C_{1-6}$ alkyl, phenyl or phenyl-$C_{1-4}$ alkyl any of which phenyl moieties may be substituted by one or more of $C_{1-6}$ alkyl, $C_{1-6}$ alkoxy, halogen or $CF_3$; and $R^2_2$ is hydrogen, or $R^2_1$ and $R^2_2$ together form an oxo group and X, Y, Z and $R_3$ are as defined in formula (I) with a dehydrating agent and thereafter if desired or necessary reacting a resulting compound of formula (I) wherein $R_1$ and $R_2$ form an oxo group with:

(i) a carbonyl reducing agent to form a compound of formula (I) wherein $R_1$ is hydrogen and $R_2$ is hydroxy;

(ii) a $C_{1-6}$ alkyl, phenyl or phenyl $C_{1-4}$ alkyl Grignard reagent or equivalent metallic complex reagent to form a compound wherein $R_1$ is other than hydrogen and $R_2$ is hydroxy; or (iii) $H_2NOR_7$ to form a compound wherein $R_1$ and $R_2$ together form $=NOR_7$ group; and thereafter if desired or necessary converting $R_2$ when hydroxy to hydrogen, $C_{1-6}$ alkoxy, phenyl $C_{1-4}$ alkoxy or $C_{1-7}$ acyloxy and/or alkylating $R_2$ when $NHR_4$ or $NH_2$ to $NR_4R_5$ or interconverting $R_2$ or forming a pharmaceutically acceptable salt.

The cyclisation reaction is normally carried out under acid conditions using a dehydrating agent such as phosphorus pentoxide. When $R^2_1$ and $R^2_2$ together form an oxo group, the reaction is normally carried out in methanesulphonic acid at room temperature. When $R^2_1$ and $R^2_2$ are both hydrogen, suitably excess phosphorus pentoxide is used, at elevated temperatures eg 100° C.

The reduction step (i) may be carried out with any of the usual carbonyl reducing agents under conditions which will be apparent to the skilled man. Suitable examples of carbonyl reducing agents are metal hydride reducing agents such as lithium aluminium hydride in an organic solvent such as tetrahydrofuran or ether, or sodium borohydride in a lower alcohol at a temperature of 0°–150° C. A particularly favoured reducing agent is lithium aluminium hydride in ether. Alternatively, the reduction may be carried out by catalytic hydrogenation.

The reaction with a Grignard reagent (ii) may take place under conditions normally used in the art for this type of reaction, for example using $R_1{}^3MgX$ wherein $R_1{}^3$ is $C_{1-6}$ alkyl, phenyl or phenyl $C_{1-4}$ alkyl and X is a halogen usually chlorine, bromine or iodine in an inert solvent such as ether or tetrahydrofuran. Other equivalent metallic complex reagents include $R_1{}^3Li$ wherein $R_1{}^3$ is as defined above, in an inert solvent.

The compound $H_2NOR_7$ is reacted with the compound of formula (I) (step (iii)) at a temperature between 0°–150° C. according to the reactivity of the compound $H_2NOR_7$ employed.

$R_2$ hydroxy groups may be converted to $C_{1-6}$ alkoxy or optionally substituted phenyl $C_{1-6}$ alkoxy groups by example, reaction with a compound $R_2{}^2L$ wherein $R_2{}^2$ is $C_{1-6}$ alkyl or phenyl $C_{1-6}$ alkyl and L is a good leaving group such as halogen or a tosylate residue, under basic conditions. Alternatively, the $R_2$ hydroxy group is converted to an alkoxide ion by the action of strong base and then reacted with $R_2L^1$ wherein $L^1$ is a halogen, suitably bromine. More usually, the convertion may be achieved by heating with $R_2{}^2OH$ and an acid such as hydrochloric acid.

$R_2$ hydroxy groups may be converted to $C_{1-7}$ acyloxy groups under acylation conditions which will be apparent to the skilled man. Suitably acylation is carried out with a $C_{1-7}$ carboxylic acid or a reactive derivative thereof in an inert solvent. Often the 'reactive derivative' will be the acid halide such as the acid chloride, in an inert solvent such as benzene or diethyl ether at 0°–50° C. Other reactive derivatives of the $C_{1-7}$ carboxylic acid include anhydrides. Optionally the reaction may be carried out under basic conditions, for example, in pyridine as solvent to facilitate the reaction where necessary.

$R_2$ hydroxy groups may be converted to hydrogen by reduction. One suitable method is to dehydrate the compound of formula (I) wherein $R_2$ is hydroxy under acid conditions and to subsequently catalytically hydrogenate the resulting olefinic double bond.

Alkylation of $NH_2$ to $NR_4R_5$ wherein one or both of $R_4$ and $R_5$ are $C_{1-6}$ alkyl, or $NHR_4$ to $NR_4R_5$ wherein $R_4$ and $R_5$ are $C_{1-6}$ alkyl may be carried out in conventional manner, for example using an excess of an $C_{1-6}$ alkyl halide in a base such as $K_2CO_3$ in a solvent such as acetone or DMF at a temperature suitably in the range 55° C. to 120° C. It will be appreciated that when $R_4$ and $R_5$ are different alkyl groups or only one of $R_4$ and $R_5$ an alkyl group unwanted alkylation of $R_4$ or $R_5$ hydrogens may be prevented by adjusting conditions accordingly. It is normally preferable, however, to alkylate by acylation followed by reduction. For example, formylation followed by reduction results in monomethylation. The reduction may be carried out under standard conditions, such as using lithium aluminium hydride in ether or tetrahydrofuran.

Other methods of interconverting $R_2$ groups will be apparent to the skilled man. For example, when $R_1$ is other then hydrogen and $R_2$ is $NR_4R_5$ in the compound of formula (I), it is desirable to prepare the corresponding compound wherein $R_2$ is hydroxy and convert this compound to a compound wherein $R_2$ is replaced by a good leaving group such as halide or an activated ester group, for example a tosylate residue and react this with a compound $HNR_4R_5$. Conditions for this reaction are those normally used in the art for these types of reactions.

The compounds of formula (VIII) are novel and thus form an aspect of the present invention as intermediates.

The invention thus also provides a process for the preparation of a compound of formula (I) wherein $R_1$ and $R_2$ and other than an oxo group which process comprises the reaction of a compound of formula (IX):

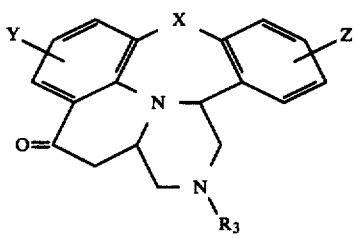

under steps (i), (ii) or (iii) as hereinbefore defined.

Intermediates of formula (VIII) may be prepared according to the following reaction sequence:

U.S. Pat. Nos. 3,534,041 and 3,701,778 or by analogous methods thereto.

The present invention also provides a pharmaceutical composition which comprises a compound of this invention and a pharmaceutically acceptable carrier.

The composition of this invention will normally and preferably be adapted for oral administration although parenteral compositions are also envisaged as useful.

The compositions of this invention will most suitably be presented as unit dose compositions containing from 1 to 200 mg, more usually from 5 to 100 mg, for example 10 to 50 mg such as 12.5, 15, 20, 25 or 30 mg. Such compositions will normally be taken from 1 to 6 times daily, for example 2, 3 or 4 times daily so that the total

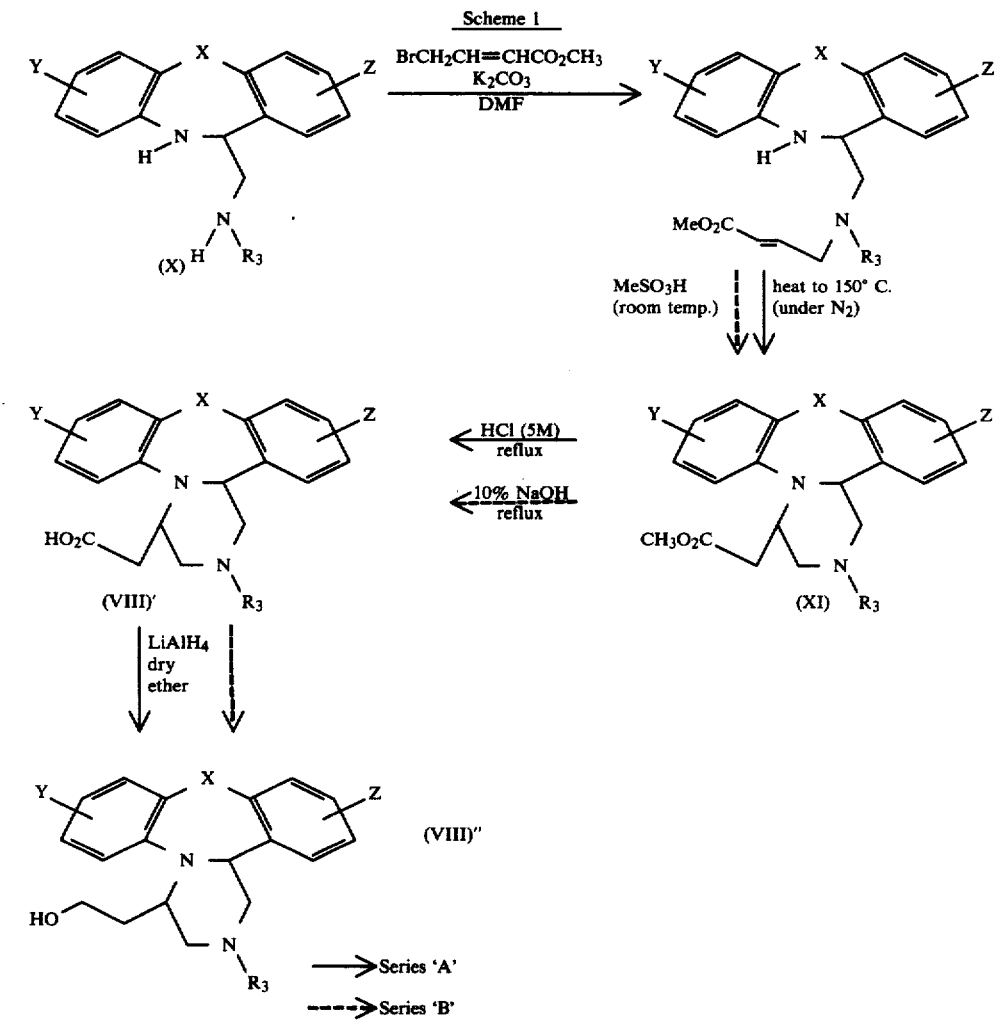

The route shown in Scheme 1 marked series 'A' involves a stereospecific cyclisation reaction so that the resulting compounds of the formulae (XI) and (VIII) are of one diastereoisomeric form only. The route marked series 'B' involves a non-stereospecific cyclisation reaction and a mixture of diastereoisomers of compounds of formula (XI) is formed. The diastereoisomers of formula (XI) may be separated by conventional methods such as column chromatography before subsequent hydrolysis to the acid (VIII).

Compounds of formula (X) may be prepared as described in U.K. Pat. Nos. 1,173,783 and 1,229,253 or amount of active agent administered is within the range 5 to 400 mg.

Preferred unit dosage forms include tablets, capsules and their equivalents.

The compositions of this invention may be formulated by conventional methods of blending, filling, compressing and the like.

Suitable carriers for use in this invention include diluents, binders, disintegrants, colouring agents, flavouring agents, preservatives and the like. These agents may be utilized in conventional manner, for example in a manner similar to that already used for other mood modifying aents such as clinically used anti-depressant and anxiolytic agents.

The invention also provides a method of treatment of CNS disorders in mammals including humans which method comprises administering an effective amount of a compound of the invention or a salt thereof to the sufferer.

The following Examples illustrate the invention.

The following Descriptions illustrate the preparation of intermediates.

DESCRIPTION 1

(a)

Methyl-4-(methylaminomethyl-5,6-dihydro-6-morphanthridinyl) but-2-enoate

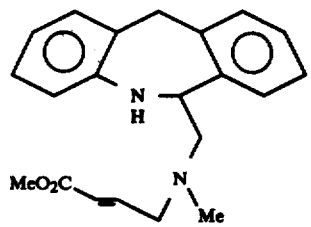

6-methylaminomethyl-5,6-dihydromorphanthridine (20 g, 0.084 mol) was dissolved in dry dimethylformamide (150 ml). To this solution, potassium carbonate (11.6 g, 0.084 mol) was added and to the resulting mixture stirred at room temperature, methyl-4 -bromocrotonate (85%, 17.6 g, 0.084 mol) was added dropwise. The reaction mixture was stirred at room temperature for 4 hours (the reaction followed by t.l.c. on silica gel eluted with diethyl ether). When t.l.c. indicated that the reaction was complete, the solvent was removed and ether (100 ml)/water (200 ml) added to the residue. The organic layer was separated and the aqueous further extracted with 2×50 ml portions of ether. The organic extracts were combined, dried (MgSO$_4$) and the solvent removed in vacuo to give a brown oil. Purification of the product was achieved by filtration through a short column of silica gel eluted with ether. The title product was obtained as a brown oil in 65% yield.

(b)

4-Carbomethoxymethyl-2-methyl-1,2,3,4,10,14b-hexahydropyrazino[1,2-f]morphanthridine (Series 'A')

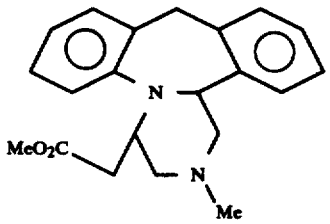

The compound prepared in (a) was heated to 150° C. with stirring under nitrogen, then kept at this temperature for a further 2-3 hours (the reaction was followed by intra-red spectroscopy until the N-H band of the starting material became insignificant). The product was then dissolved in ether and filtered through a short column of silica gel. Removal of the solvent gave the title compound in 65% yield as a brown oil.

A sample was converted to the hydrochloride salt and recrystallised from methanol/ether to give white crystals m.p. 259°-262° C.

(c)

4-Carboxymethyl-2-methyl-1,2,3,4,10,14b-hexahydropyrazino [1,2-f]morphanthridine hydrochloride (Series 'A')

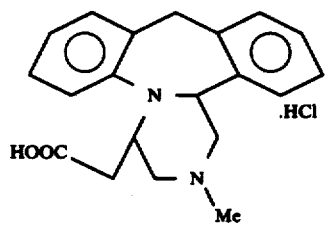

The ester prepared in (b) (10 g) was heated under reflux in 5 N hydrochloric acid (150 ml) for 2 hours. On cooling, the hydrochloride salt of the title acid precipitated as a white solid. After filtration, washing with water and drying in a vacuum oven, the yield of the title compound was 90%. Recrystallisation from acetone gave the title compound as an off white solid (m.p. 268°-270° C.).

DESCRIPTION 2

(a)

4-Carbomethoxymethyl-2-methyl-1,2,3,4,10-14b-hexahydropyrazino[1,2-f]morphanthridine (Series 'B')

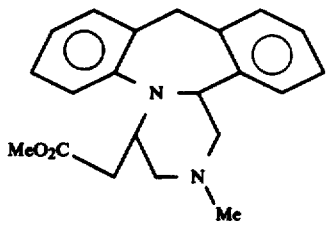

Methyl-4-(methylaminomethyl-5,6-dihydro-6-morphanthridinyl)but-2-enoate (1.5 g) (description 1a) was dissolved in methanesulphonic acid (20 ml) and the resulting solution stirred at room temperature for 1 hour. The reaction mixture was poured onto ice/water basified with sodium hydroxide and extracted with ethyl acetate (3×25 ml). Removal of the solvent in vacuo gave a brown oil which was purified by column chromatography on silica gel eluted with ether.

0.25 g (35%) of ester diastereomer A was isolated, 0.78 g (52%) of ester diastereomer B was isolated.

Ester B was converted to the hydrochloride salt and recrystallized from methanol/ether to give white crystals mp 231°-234° C.

| | Analysis | |
|---|---|---|
| | Calc. | Found |
| N | 7.52 | 7.47 |
| C | 67.65 | 67.40 |
| H | 6.71 | 6.86 |
| Cl | 9.53 | 9.31 |

(b)
4-Carboxymethyl-2-methyl-1,2,3,4,10,14b-hexahydropyrazino[1,2-f]morphanthridine hydrochloride (Series 'B')

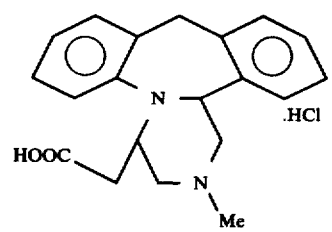

The ester prepared in (a) (5 g) was heated under reflux in 10% sodium hydroxide for 2 hours. The reaction mixture was then acidified with 5 N hydrochloric acid. As the solution cooled the hydrochloride salt of the acid precipitated as a white solid. The solid was filtered, washed with water and dried in a vacuum oven. After drying the yield was 85%, mp 295°–299° C.

DESCRIPTION 3

4-(2-hydroxyethyl)-2-methyl-1,2,3,4,10,14b hexahydropyrazino morphanthridine (Series 'B')

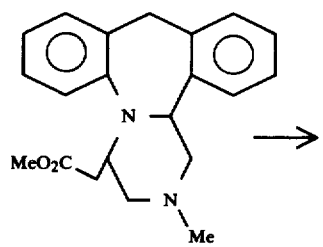

→

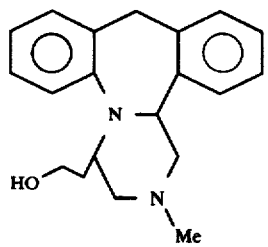

The ester (5 g) was dissolved in dry diethyl ether (10 ml) and excess lithium aluminium hydride (0.6 g) was added in portions to the stirred mixture. The reaction mixture was stirred at room temperature for 30 mins until tlc (silica gel/ether) indicated no ester remained.

Water (0.6 ml), 15% sodium hydroxide (0.6 ml) and water (1.8 ml) were added and the mixture filtered. Removal of the solvent gave the alcohol in 45% yield as a white solid.

Recrystallisation from ethyl acetate/60°–80° petroleum ether gave white crystals mp 138°–140° C.

| Analysis | Calc. | Found |
|---|---|---|
| C | 77.92 | 77.71 |
| H | 7.79 | 8.07 |
| N | 9.09 | 9.01 |

DESCRIPTION 4

(a)
5(3′-methoxycarbonylprop-2′-enyl-methylamino)methyl-2,3,6,7-dibenzo[1,4]oxazepin Compound was prepared as outlined in Description 1(a).

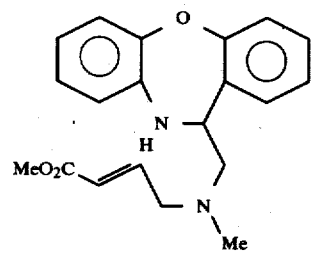

purified on column chromatography, silica gel eluted with ether obtained as brown oil in 69% yield.

(b)
4-carbomethoxymethyl-2-methyl-1,3,4,14b-tetrahydro-2H-dibenzo-(b,f)-pyrazino(1,2-d)(1,4)oxapin

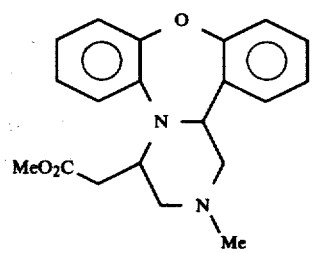

Compound was prepared in a similar way to that described for Description 1(b) and was obtained in 82% yield, converted to the maleate salt and recrystallised from methanol/ether mp 158°–160° C.

| Analysis | Calc. | Found |
|---|---|---|
| C | 63.44 | 63.21 |
| H | 5.73 | 5.87 |
| N | 6.16 | 6.03 |

DESCRIPTION 5

4-(2-hydroxyethyl)-2-methyl-1,3,4,14b-tetrahydro-2H-dibenzo-(b,f)-pyrazino[1,2-d][1,4]-oxazepin In a similar manner to Description 4 the title compound was prepared.

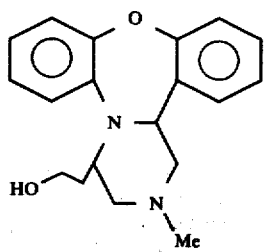

Column chromatography on silica gel eluted with ethyl acetate gave the required product in 63% yield.

Sample recrystallised from ethyl acetate/ether had melting point 138°–139° C.

| Analysis | Calc. | Found |
|---|---|---|
| C | 73.55 | 73.56 |
| H | 7.09 | 7.13 |
| N | 9.03 | 8.92 |

EXAMPLE 1A 1,2,3,3a,4,5,9,13b-Octahydro-2-methyl-2-benzazepino[4,3,2-ij]pyrazino[1,2-a]quinolin-5-one (Series 'A')

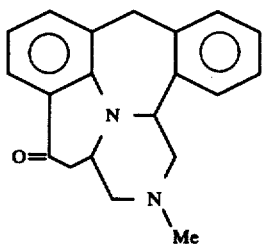

(1A)

The acid prepared in (c) (1.2 g, 0.0033 mol) was dissolved in methanesulphonic acid (12 g) and phosphorus pentoxide (2.4 g, 0.016 mol) was added in portions, with cooling. The reaction mixture was stirred at room temperature for 3 days then poured onto ice/water, basified with sodium hydroxide and extracted with ethyl acetate (3×25 ml). The organic extracts were combined, washed with water (2×20 ml) dried (MgSO$_4$.H$_2$O) and the solvent removed in vacuo and the crude ketone was obtained as an off white foam. Column chromatography on silica gel eluted with ether together with increasing proportion of ethyl acetate, gave the title compound as a white foam in 45% yield. This was converted to the hydrochloride salt and recrystallised from ethanol, m.p. 289°–291° C.

EXAMPLE 1B 1,2,3,3a,4,5,9,13b-Octahydro-2-methyl-2-benzazepino[4,3,2-ij]pyrazino[1,2-a]quinolin-5-one (Compound 2)

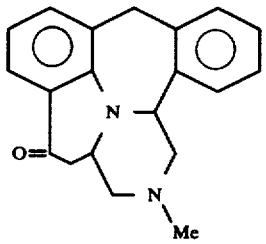

(2)

In a similar manner to Example 1A the title compound was prepared from the compound of description 2b in 53% yield.

The thus formed ketone was converted to the maleate salt which after recrystallisation from methanol/ether had a melting point of 176°–179° C.

| Analysis | Calc. | Found |
|---|---|---|
| N | 6.66 | 6.57 |
| C | 68.57 | 68.47 |
| H | 5.71 | 5.88 |

EXAMPLE 2A 1,2,3,3a,4,5,9,13b-Octahydro-2-methyl-2-benzazepino[4,3,2-ij]pyrazino[1,2-a]quinolin-5-ol (Compounds 3 and 4)

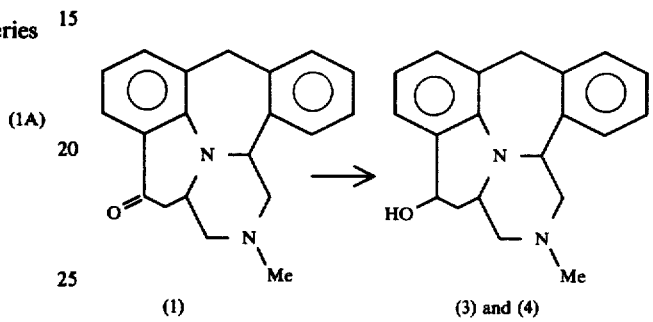

(1)     (3) and (4)

The ketone (13 g, 0.042 m) was dissolved in dry ether (150 ml) and lithium aluminium hydride (0.8 g, 0.02 m) was added in portions. The reaction mixture was stirred at room temperature for 30 minutes until t.l.c. indicated that no ketone remained.

Water (0.8 ml), 15% sodium hydroxide (0.8 ml) and water (2.4 ml) were added and the mixture filtered. (The collected inorganic solid was washed several times with ethyl acetate.) The filtrate was concentrated in vacuo and the product purified by silica gel column chromatography using ethyl acetate with increasing proportions of ethanol as eluant. Both possible epimeric alcohols (3) and (4) obtained (ratio 90%:10%). Mass spectrum m/e 306, fragmentation patterns identical.

The major product (3) was isolated in 85% yield as a white solid m.p. 160°–161° C. after recrystallisation from a mixture of ethyl acetate and ether.

| Analysis | Calc. | Found |
|---|---|---|
| N | 9.15 | 9.10 |
| C | 78.43 | 78.05 |
| H | 7.19 | 7.44 |

Compound 4

Treatment of compound 3 in dilute hydrochloric acid gave the other epimeric alcohol (4) in 35% yield, recrystallised from ether mp 161°–163° C.

| Analysis | Calc. | Found |
|---|---|---|
| C | 78.43 | 78.60 |
| H | 7.19 | 7.29 |
| N | 9.15 | 9.34 |

EXAMPLE 2B 1,2,3,3a,4,5,9,13b-Octahydro-2-methyl-2-benzazepino[4,3,2-ij]pyrazino[1,2-a]quinolin-5-ol (5)

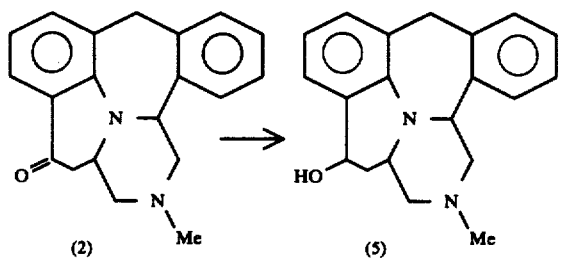

In a similar manner to example 2A the title compound was prepared from compound 2.

The alcohol was converted to the maleate salt which after recrystallization from methanol/ether had a melting point of 191°-193° C.

EXAMPLE 3A 1,2,3,3a,4,5,9,13b Octahydro-2-methyl-2-benzazepino[4,3,2-ij]pyrazino[1,2-a]quinoline (compound 6)

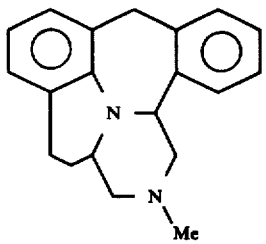

The alcohol of example 2A (8 g, 0.026 mol) was dissolved in benzene (100 ml) and toluene-4-sulphonic acid (9.9 g, 0.052 mol) added. The reaction mixture was refluxed using a Dean and Stark trap to remove water. Reflux was continued until t.l.c. (silica gel/ether) indicated no alcohol remained. The organic layer was washed twice with saturated sodium bicarbonate solution (2×25 ml), dried (MgSO₄) and the solvent removed in vacuo to give a brown oil in 99% yield. This product was hydrogenated at atmospheric pressure in ethyl acetate using 10% palladium on charcoal as catalyst until hydrogen uptake had ceased.

The catalyst was filtered off and the solvent removed in vacuo to give a brown solid.

Column chromatography on silica gel eluted with ether together with increasing proportion of ethyl acetate gave the title compound as a white solid in 23% yield. This was converted to the maleate salt and recrystallized from methanol/ether to give white crystals. mp 189°-191° C.

Mass Spectrum m/e 290.

| Analysis | Calc. | Found |
|---|---|---|
| C | 70.93 | 70.86 |
| H | 6.40 | 6.66 |
| N | 6.89 | 6.51 |

EXAMPLE 3B 1,2,3,3a,4,5,9,13b-octahydro-2-methyl-2-benzazepino[4,3,2-ij]pyrazino[1,2-a]quinoline (Compound 7)

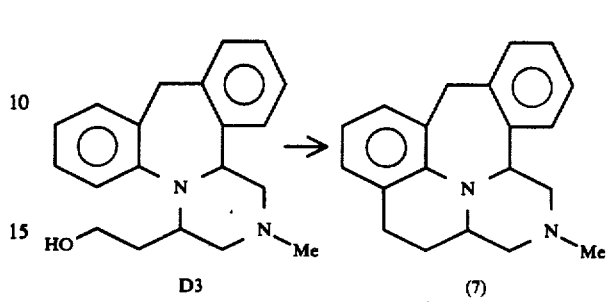

Alcohol (0.4 g) was heated in excess polyphosphoric acid at 100° C. for 2 hours. The reaction mixture was poured onto ice/water and basified with 40% sodium hydroxide. The pentacyclic product was extracted into ethyl acetate.

Column chromatography on silica gel eluted with ethyl acetate gave the required product in 76% yield as a brown oil.

This was converted to the maleate salt which after recrystallisation from methanol/diethyl ether had a melting point 159°-162° C. Mass spectrum m/e 290 fragmentation pattern identical to compound 6.

| Analysis | Calc. | Found |
|---|---|---|
| C | 70.93 | 71.02 |
| H | 6.40 | 6.49 |
| N | 6.89 | 6.76 |

EXAMPLE 4B 1,2,3,3a,4,5,9,13b-octahydro-2-methyl-2-benzazepino[4,3,2-ij]-pyrazino[1,2-a]-5-oxaminoquinoline (Compound 8)

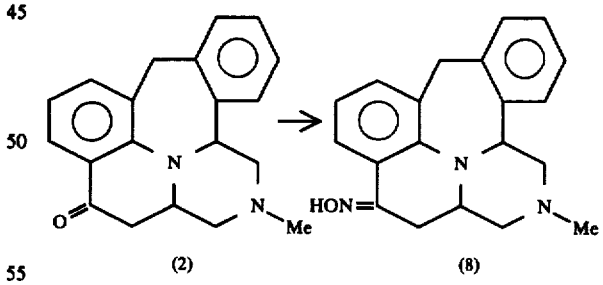

To a mixture of ketone (1 g, 0.0032 mol), hydroxylamine hydrochloride (0.35 g, 0.005 mol), ethanol (2 ml) and water (0.5 ml) was added sodium hydroxide (0.65 g, 0.016 mol) in portions. The resulting mixture was refluxed for 10 mins and then extracted with ethyl acetate. The crude product, purified by column chromatography on silica gel eluted with ether, was obtained as a white solid in 58% yield mp 216°-219° C.

A sample was converted to the maleate salt and after recrystallisation from acetone/ether had melting point 164°-166° C.

Mass spectrum m/e 319.

| Analysis | Calc. | Found |
|---|---|---|
| C | 66.20 | 65.43 |
| H | 5.75 | 6.06 |
| N | 9.65 | 8.94 |

EXAMPLE 5B 1,2,3,3a,4,5,9,13b-octahydro-2-methyl-2-benzazepino[4,3,2-ij]-pyrazino[1,2-a]-5-hydroxy-5-phenylquinoline (Compound 9)

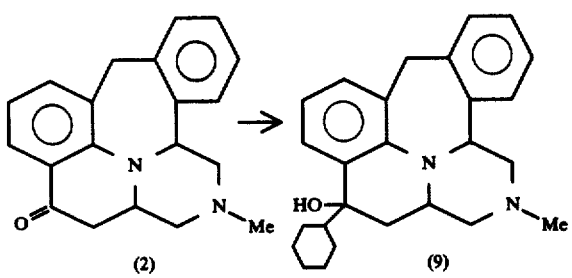

Phenylmagnesium bromide was prepared from bromobenzene (0.78 g, 0.005 mol) and magnesium (0.12 g, 0.005 mol) using dry THF as solvent. To this mixture was added the ketone (0.5 g, 0.0016 mol) in dry THF. The reaction mixture was stirred at room temperature for 2 hours before ammonium chloride was added and the product extracted into ethyl acetate. Column chromatography on silica gel eluted with ether gave the desired compound which was converted to the maleate salt and recrystallised from acetone/ether in 33% yield with melting point 220°-202° C.

Mass spectrum m/e 382.

| Analysis | Calc. | Found |
|---|---|---|
| C | 72.29 | 71.94 |
| H | 6.02 | 5.79 |
| N | 5.62 | 5.61 |

EXAMPLE 6A 1,2,3,3a,4,5,9,13b-octahydro-2-methyl-2-benzazepino[4,3,2,-ij]pyrazino[1,2-a]-5-dimethylaminoquinoline

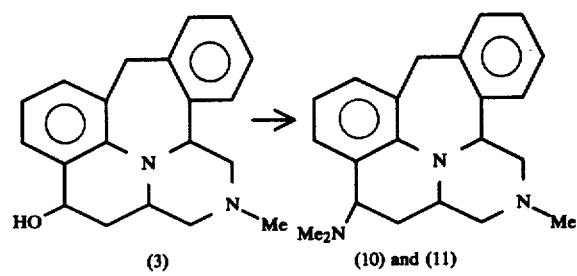

Alcohol (2 g, compound 3) was dissolved in dichloromethane (40 ml) and triethylamine (1 ml) added. The solvent was cooled to −10° C. using dry ice/acetone bath and methanesulphonyl chloride (0.5 ml) was added keeping the reaction mixture at −10° C.

The mixture was allowed to rise to 0° C. over approx. 30 mins then excess dimethylamine solution in 1 MS was added. The solution was stirred at 0° C. for 15 mins, then allowed to stir at room temperature overnight.

Column chromatography on silica gel eluted with ether gave the two epimeric amines (ratio 75%:25%). Mass spectrum fragmentation patterns identical.

Compound 10

The major product was isolated in 57% yield as an off-white solid, recrytallised from ether with melting point 128°-130° C.

| Analysis | Calc. | Found |
|---|---|---|
| C | 79.28 | 79.00 |
| H | 8.11 | 8.22 |
| N | 12.61 | 12.59 |

Compound 11

The minor product was obtained in 19% yield recrystallised from ethyl acetate/60°-80° petroleum ether and had melting point 136°-138° C.

| Analysis | Calc. | Found |
|---|---|---|
| C | 79.28 | 79.54 |
| H | 8.11 | 8.36 |
| N | 12.61 | 12.57 |

EXAMPLE 7A 1,2,3,3a,4,5,9,13b-octahydro-2-methyl-2-benzazepino[4,3,2-ij]pyrazino[1,2-a]-5-morpholinoquinoline (Compound 12)

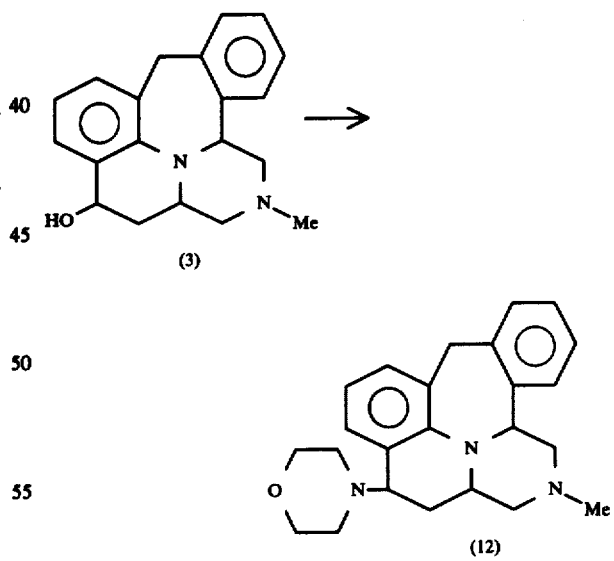

In a similar manner the title compound was prepared from compound 3 of Example 2A.

The product was obtained in 28% yield after column chromatography on silica gel eluted with ether and had melting point 197°-199° C.

| Analysis | Calc. | Found |
|---|---|---|
| C | 76.80 | 76.55 |
| H | 7.73 | 7.75 |

| Analysis | Calc. | Found |
|---|---|---|
| N | 11.20 | 11.17 |

EXAMPLE 8A 1,2,3,3a,4,5,9,13b-octahydro-2-methyl-2-benzazepino[4,3,2-ij]-pyrazino[1,2-a]-5-methoxyquinoline (Compounds 12 and 13)

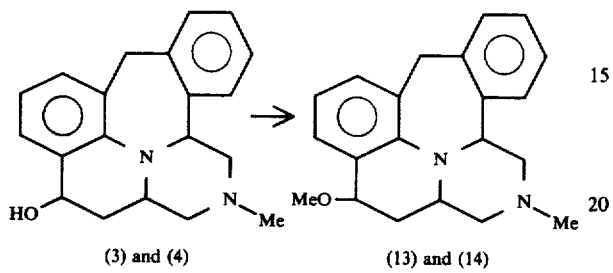

(3) and (4)    (13) and (14)

A mixture of the two 'A' series alcohols (compounds 3 and 4) was treated with a methanol/dilute hydrochloric acid mixture at room temperature until tlc (silica gel/ether) indicated no starting alcohol remained. The reaction mixture was evaporated to dryness, basified and extracted with ether. Column chromatography on silica gel eluted with ether gave the two possible epimeric methoxy derivatives (ratio 2:1). Both had mass spectrum m/e 320 with identical fragmentation patterns.

The major product (13) was converted to the maleate salt and recrystallised from acetone/ether in 32% yield and had melting pint 168°-171° C.

| Analysis | Calc. | Found |
|---|---|---|
| C | 68.81 | 68.53 |
| H | 6.41 | 6.30 |
| N | 6.42 | 6.34 |

EXAMPLE 9A 1,2,3,3a,4,5,9,13b-octahydro-2-methyl-2-benzazepino[4,3,2-ij]-pyrazino[1,2-a]-5-acetoxyquinoline (Compound 15)

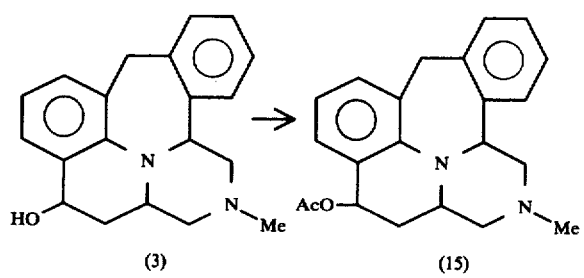

(3)    (15)

The alcohol of Example 2A, Compound 3 (0.5 g) was dissolved in pyridine (10 ml) and acetic anhydride (10 ml) added dropwise. The mixture was stirred at room temperature overnight, basified and extracted with ethyl acetate. The organic extract was washed well with water, dried (MgSO₄), and the solvent removed to give a brown oil. Column chromatography on silica gel eluted with ether gave the title compound as white crystals in 37% yield.

The acetoxy analogue was converted to the maleate salt which after recrystallization from acetone/ether had melting point of 161°-164° C.

| Analysis | Calc. | Found |
|---|---|---|
| C | 67.24 | 67.05 |
| H | 6.03 | 6.08 |
| N | 6.03 | 5.90 |

EXAMPLE 10A 2-methyl,1,3,4,14b-tetrahydro 4,6-ethano-2H-dibenzo[bf]pyrazino[1,2-d][1,4]oxazepin-15-one (Compound 16)

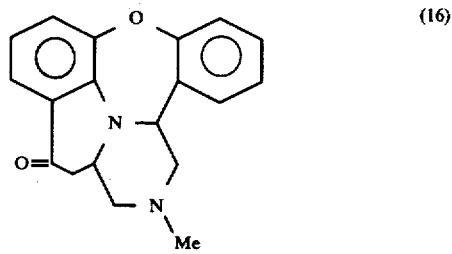

(16)

In a similar manner to Example 1A the title compound was obtained in 39% yield, converted to the maleate salt and recrystallised from acetone/ether. mp 187°-188° C.

| Analysis | Calc. | Found |
|---|---|---|
| C | 65.40 | 65.10 |
| H | 5.21 | 5.11 |
| N | 6.64 | 6.53 |

EXAMPLE 11A 2-methyl,1,3,4,14b-tetrahydro 4,6-ethano-2H-dibenzo[bf]-pyrazino[1,2-d][1,4]oxazepin-15-ol (Compounds 17 and 18)

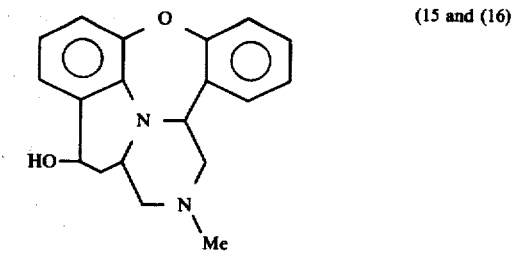

(15 and (16)

In a similar manner to Example 2A the compound 16 was converted into the two epimeric alcohols (ratio compound 17: compound 18 was 63%:37%. Major isomer (54% yield) recrystallised from ether. mp 113°-115° C.

| Analysis | Calc. | Found |
|---|---|---|
| C | 74.02 | 73.59 |
| H | 6.49 | 6.71 |

-continued

| Analysis | Calc. | Found |
|---|---|---|
| N | 9.09 | 8.71 |

Compound 16

Minor isomer (32% yield) recrystallised from ether. mp 95°-98° C.

| Analysis | Calc. | Found |
|---|---|---|
| C | 74.02 | 73.85 |
| H | 6.49 | 6.74 |
| N | 9.09 | 8.78 |

EXAMPLE 12B 2-methyl,1,3,4,14b-tetrahydro-4,6-ethano-2H-dibenzo[bf]-pyrazino[1,2-d][1,4]oxazepin (Compound 19)

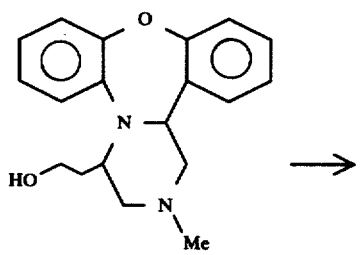

(19)

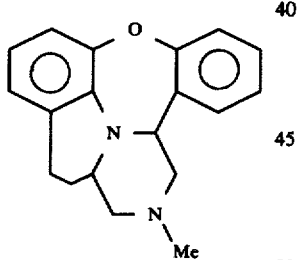

In a similar manner to Example 3B the alcohol of Description 5 was heated in PPA at 100° C. for 2 hours. The product was purified on silica gel column eluted with ether and obtained in 26% yield. It was converted to the maleate salt and recrystallised from acetone/ether as white crystals. mp 173°-176° C.

| Analysis | Calc. | Found |
|---|---|---|
| C | 67.65 | 67.37 |
| H | 5.88 | 5.85 |
| N | 6.86 | 6.72 |

EXAMPLE 13A 2-methyl,1,3,4,14b-tetrahydro 4,6-ethano-2H-dibenzo[bf]-pyrazino[1,2-d][1,4]thiapin-15-one (Compound 20)

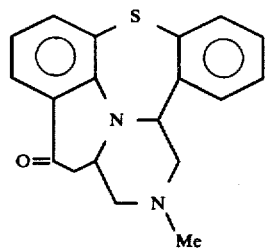

(20)

The title compound was prepared in a similar manner to that outlined in Example 1A. The ketone was obtained in 44% yield, converted to maleate salt and recrystallised from acetone/ether. mp 179°-180° C.

| Analysis | Calc. | Found |
|---|---|---|
| C | 63.01 | 62.90 |
| H | 5.02 | 5.03 |
| N | 6.39 | 6.31 |

EXAMPLE 14A 2,5-dimethyl,1,3,4,14b-tetrahydro 4,b-ethane-2H-dibenzo[bf]pyrazino[1,2-d][1,4]diazepin-15-one (Compound 21)

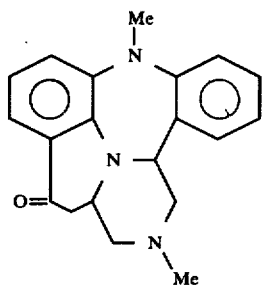

(21)

The ketone is prepared in an analogous manner to that outlined in Example 1A.

Reduction of the ketone in an analogous manner to that described in Example 2A gives the corresponding alcohol (Compound 22).

PHARMACOLOGICAL DATA

Compounds of the invention inhibit the behavoural symptoms induced by 5-methoxy-N,N-dimethyl tryptamine, a central 5-hydroxytryptamine agonist, and are central 5HT antagonists. As such they would be expected to possess anti-depressant, (Orgen, S O, Furce, K Agnati, L F, Gustofoson J A, Jonsson, G, and Holan A C, 1979, J Neural Erous, 46, 85-103) and/or anxiolytic (Stein, L, Wline, D, and Bellugi, J D, 1975, in Advance-Biochemical Psychopharmacology, ed Corta, E, and Greengord, P, Vol 14, 29-44, Rouen Press, N.Y.) activity.

Method

Mice ( δ CD⁻¹ Charles Rine) are pretreated with the compounds 10 animals/group under investigation and 1 h later one group is injected with 10 mg/kg ip 5-methoxy-N,N-dimethyltryptamine (Sigma). The symptoms of forepaw tapping movements, head jerks and splayed limbs are scored: 1, present; 0, absent, giving a maximum score of 3/mouse or 30/group. Results are expressed as the percentage inhibition compared to the group treated with 5-methoxy-N,N-dimethyl tryptamine alone. The dose of compound inhibiting the symptoms by 50% is determined graphically.

The reesults are shown in Table 1.

Toxicity

No toxic effects were observed in the above tests.

TABLE 1

| Compound No. | ED$_{50}$ mg/kg (p.o.) |
|---|---|
| 1 | 12 |
| 3 | 0.65 |
| 4 | 0.3 (i.p.) |
| 6 | 10 |
| 7 | 13 |
| 8 | 3 |
| 16 | 10 |

We claim:

1. A compound of formula (I) or a pharmaceutically acceptable salt thereof:

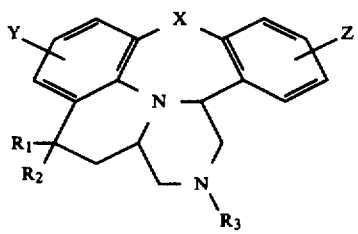

wherein:
X is $CH_2$, O, S or NR wherein R is hydrogen or $C_{1-4}$ alkyl;
Y and Z are independently selected from hydrogen, $C_{1-4}$ alkyl, $C_{1-4}$ alkoxy, halogen or $CF_3$;
$R_1$ is hydrogen, $C_{1-6}$ alkyl, phenyl or phenyl-$C_{1-4}$ alkyl any of which phenyl moieties may be substituted by one or more of $C_{1-6}$ alkyl, $C_{1-6}$ alkoxy, halogen or $CF_3$;
$R_2$ is hydrogen, OH, $C_{1-6}$ alkoxy, phenyl-$C_{1-4}$ alkoxy, $C_{1-7}$ acyloxy or $NR_4R_5$ wherein $R_4$ and $R_5$ are independently selected from hydrogen or $C_{1-6}$ alkyl; $R_4$ is hydrogen and $R_5$ is OH or $C_{1-4}$ alkoxy; or $R_4$ and $R_5$ together form $C_{3-6}$ polymethylene optionally interrupted by one O or one $NR_6$ where $R_6$ is hydrogen or $C_{1-4}$ alkyl; or together with $R_1$ forms an oxo group or $=NOR_7$ wherein $R_7$ is hydrogen or $C_{1-6}$ alkyl; and
$R_3$ is hydrogen or $C_{1-6}$ alkyl.

2. A compound according to claim 1 wherein $R_3$ is methyl.

3. A compound of formula (II):

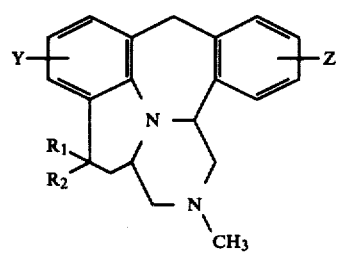

wherein
Y and Z are independently selected from hydrogen, $C_{1-4}$ alkyl, $C_{1-4}$ alkoxy, halogen or $CF_3$;
$R_1$ is hydrogen, $C_{1-6}$ alkyl, phenyl or phenyl-$C_{1-4}$ alkyl any of which phenyl moieties may be substituted by one $C_{1-6}$ alkyl, $C_{1-6}$ alkoxy, halogen or $CF_3$; and
$R_2$ is hydrogen, OH, $C_{1-6}$ alkoxy, phenyl-$C_{1-4}$ alkoxy, $C_{1-7}$ acyloxy or $NR_4R_5$ wherein $R_4$ and $R_5$ are independently selected from hydrogen or $C_{1-6}$ alkyl; $R_4$ is hydrogen and $R_5$ is OH or $C_{1-4}$ alkoxy; or $R_4$ and $R_5$ together form $C_{3-6}$ polymethylene optionally interrupted by one O or one $NR_6$ where $R_6$ is hydrogen or $C_{1-4}$ alkyl; or together with $R_1$ forms an oxo group or $=NOR_7$ wherein $R_7$ is hydrogen or $C_{1-6}$ alkyl.

4. A compound of the formula (III):

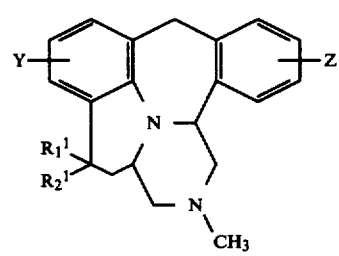

wherein:
$R_1^1$ is hydrogen, methyl, phenyl or benzyl;
$R_2^1$ is hydroxy, methoxy, acetoxy or benzyloxy; and
Y is hydrogen, $C_{1-4}$ alkyl, $C_{1-4}$ alkoxy, halogen or $CF_3$.

5. 1,2,3,3a,4,5,9,13b-Octahydro-2-methyl-2-benzazepino[4,3,2-ij]pyrazino[1,2-a]quinolin-5-ol.

6. The 'A' series diastereoisomer of 1,2,3,3a,4,5,9,13b-octahydro-2-methyl-2-benzazepino[4,3,2-ij]pyrazino[1,2-a]-quinolin-5-ol.

7. An anti-depressant or anxiolytic pharmaceutical composition which comprises an anti-depressant or anxiolytic effective amount of a compound according to claim 1 or a pharmaceutically acceptable salt thereof, and a pharmaceutically acceptable carrier.

8. A method of treating CNS disorders in mammals including humans which method comprises administering an anti-depressant or anxiolytic effective amount of a compound according to claim 1 or a pharmaceutically salt thereof to the sufferer.

* * * * *